US012611090B2

(12) United States Patent
Chu et al.

(10) Patent No.: US 12,611,090 B2
(45) Date of Patent: Apr. 28, 2026

(54) ENDOSCOPIC DEVICE WITH USB PORT AND POWERED ACCESSORIES

(71) Applicant: Boston Scientific Scimed, Inc., Maple Grove, MN (US)

(72) Inventors: Michael S.H. Chu, Brookline, MA (US); Joseph Arruda, Taunton, MA (US); Sacha Tang, Tygnsborough, MA (US); Kenneth W. Adams, Maynard, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/429,724

(22) Filed: Feb. 1, 2024

(65) Prior Publication Data

US 2024/0164625 A1 May 23, 2024

Related U.S. Application Data

(63) Continuation of application No. 16/948,027, filed on Aug. 27, 2020, now Pat. No. 11,918,186.

(Continued)

(51) Int. Cl.
*A61B 1/00* (2006.01)
*A61B 1/005* (2006.01)
(Continued)

(52) U.S. Cl.
CPC ........ *A61B 1/0016* (2013.01); *A61B 1/00098* (2013.01); *A61B 1/00135* (2013.01);
(Continued)

(58) Field of Classification Search
CPC ........... A61B 2018/00511; A61B 2018/00595; A61B 2018/0066; A61B 2017/00323;
(Continued)

(56) References Cited

U.S. PATENT DOCUMENTS 4,178,920 A * 12/1979 Cawood, Jr. ...... A61M 25/0147
74/502
5,159,446 A * 10/1992 Hibino ............... A61B 1/00042
600/152

(Continued)

FOREIGN PATENT DOCUMENTS

CN 108095787 A 6/2018
JP S57117824 A 7/1982
JP 4047563 B2 2/2008

OTHER PUBLICATIONS

Office Action in Chinese Application No. 202080067147.6, dated Nov. 6, 2024 (5 pages).

(Continued)

*Primary Examiner* — Michael J Carey
*Assistant Examiner* — Megan Elizabeth Monahan
(74) *Attorney, Agent, or Firm* — Bookoff McAndrews, PLLC

(57) ABSTRACT

An endoscopic deployment device includes a body mountable on an endoscopic device, a communication interface, and a motor. The body has a movable carrier couplable to an elongated end effector device. The effector device has an end effector shaft covered by an outer sheath and an end effector extending from a distal end of the shaft. The sheath is sized and shaped for insertion through a working channel of an endoscopic shaft of the endoscopic device. The body has a carrier channel sized for the carrier to slide therein. The end effecter is actuatable between open and closed positions by sliding the carrier in the carrier channel which in turn slides the sheath over the end effector shaft to uncover/cover the end effector. Rotation of a drive shaft of the motor is sliding the carrier in the carrier channel and actuating the end effector in response to a signal.

16 Claims, 11 Drawing Sheets

Related U.S. Application Data

(60) Provisional application No. 62/904,909, filed on Sep. 24, 2019.

(51) Int. Cl.

| | |
|---|---|
| *A61B 17/221* | (2006.01) |
| *A61B 18/22* | (2006.01) |
| *A61B 1/307* | (2006.01) |
| *A61B 17/00* | (2006.01) |
| *A61B 18/00* | (2006.01) |

(52) U.S. Cl.
CPC .......... *A61B 1/0052* (2013.01); *A61B 1/0057* (2013.01); *A61B 17/221* (2013.01); *A61B 18/22* (2013.01); *A61B 1/307* (2013.01); *A61B 2017/00323* (2013.01); *A61B 2017/00398* (2013.01); *A61B 2018/00511* (2013.01); *A61B 2018/00595* (2013.01); *A61B 2018/0066* (2013.01)

(58) Field of Classification Search
CPC .......... A61B 2017/00398; A61B 18/22; A61B 17/221; A61B 1/0016; A61B 1/00098; A61B 1/00135; A61B 1/0052; A61B 1/0057; A61B 1/307
See application file for complete search history.

(56) References Cited

U.S. PATENT DOCUMENTS

| | | | | |
|---|---|---|---|---|
| 7,846,107 | B2 * | 12/2010 | Hoffman ................ | A61B 10/06 |
| | | | | 600/561 |
| 2001/0004676 | A1 * | 6/2001 | Ouchi ................ | A61B 1/00133 |
| | | | | 606/1 |
| 2007/0225562 | A1 | 9/2007 | Spivey et al. | |
| 2010/0217075 | A1 * | 8/2010 | Shigeta .............. | G02B 23/2484 |
| | | | | 600/104 |
| 2012/0238814 | A1 | 9/2012 | Ashida et al. | |
| 2015/0230697 | A1 | 8/2015 | Phee et al. | |
| 2018/0071481 | A1 | 3/2018 | Snoke et al. | |
| 2019/0142247 | A1 * | 5/2019 | Maeda ................... | A61B 1/018 |
| | | | | 600/106 |

OTHER PUBLICATIONS

Extended Search Report in European Application No. 25161071.3, dated Jun. 12, 2025 (9 pages).

* cited by examiner

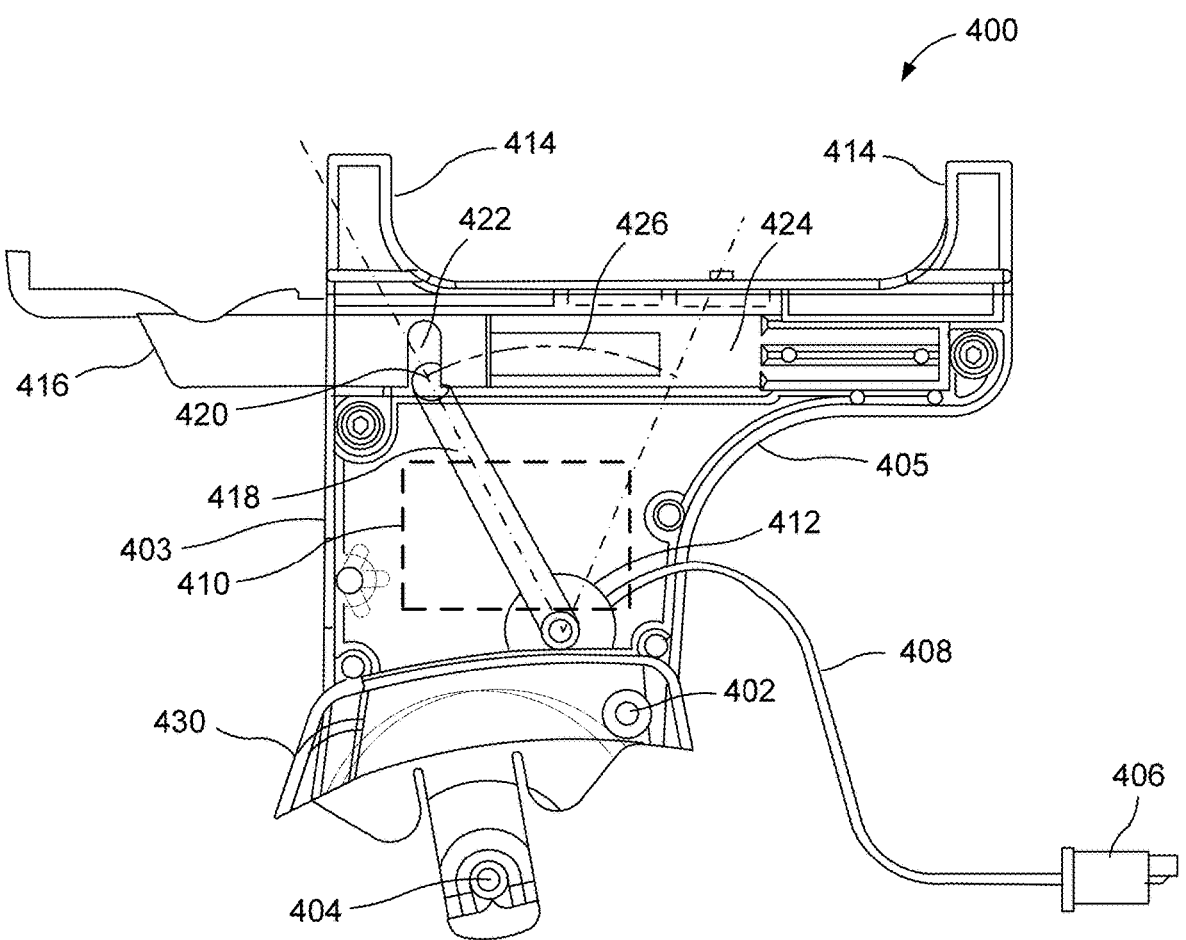
F I G. 4A

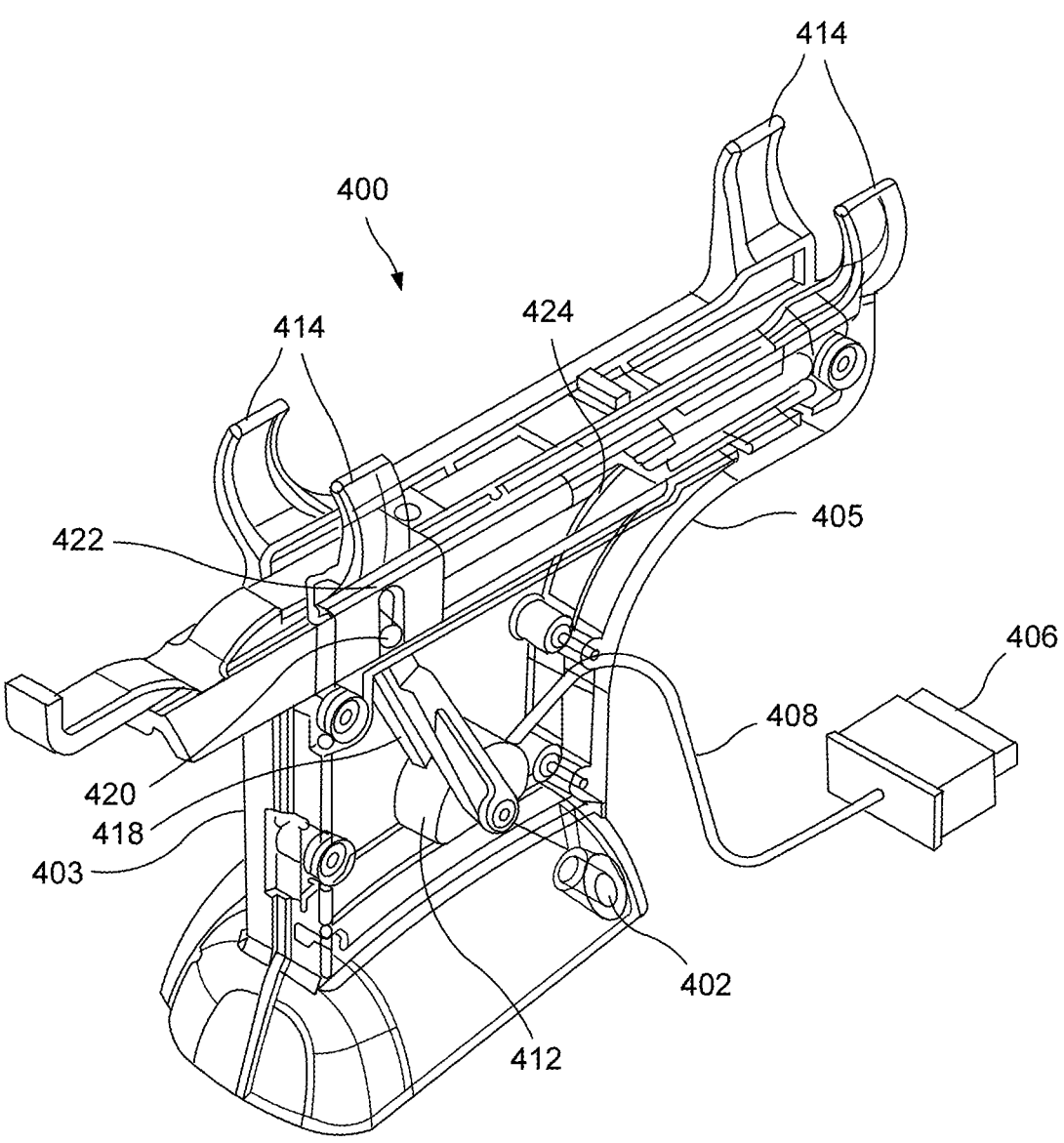
F I G. 4B

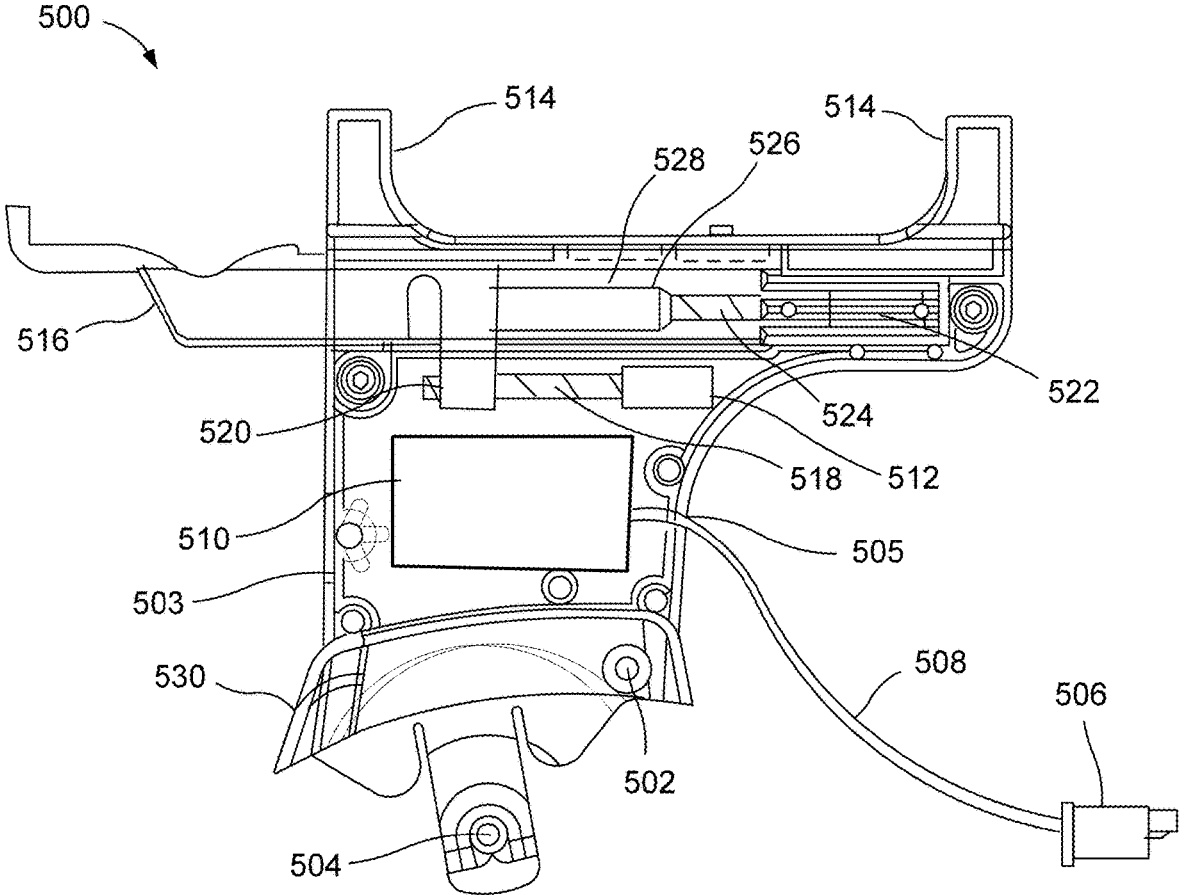
F I G. 5A

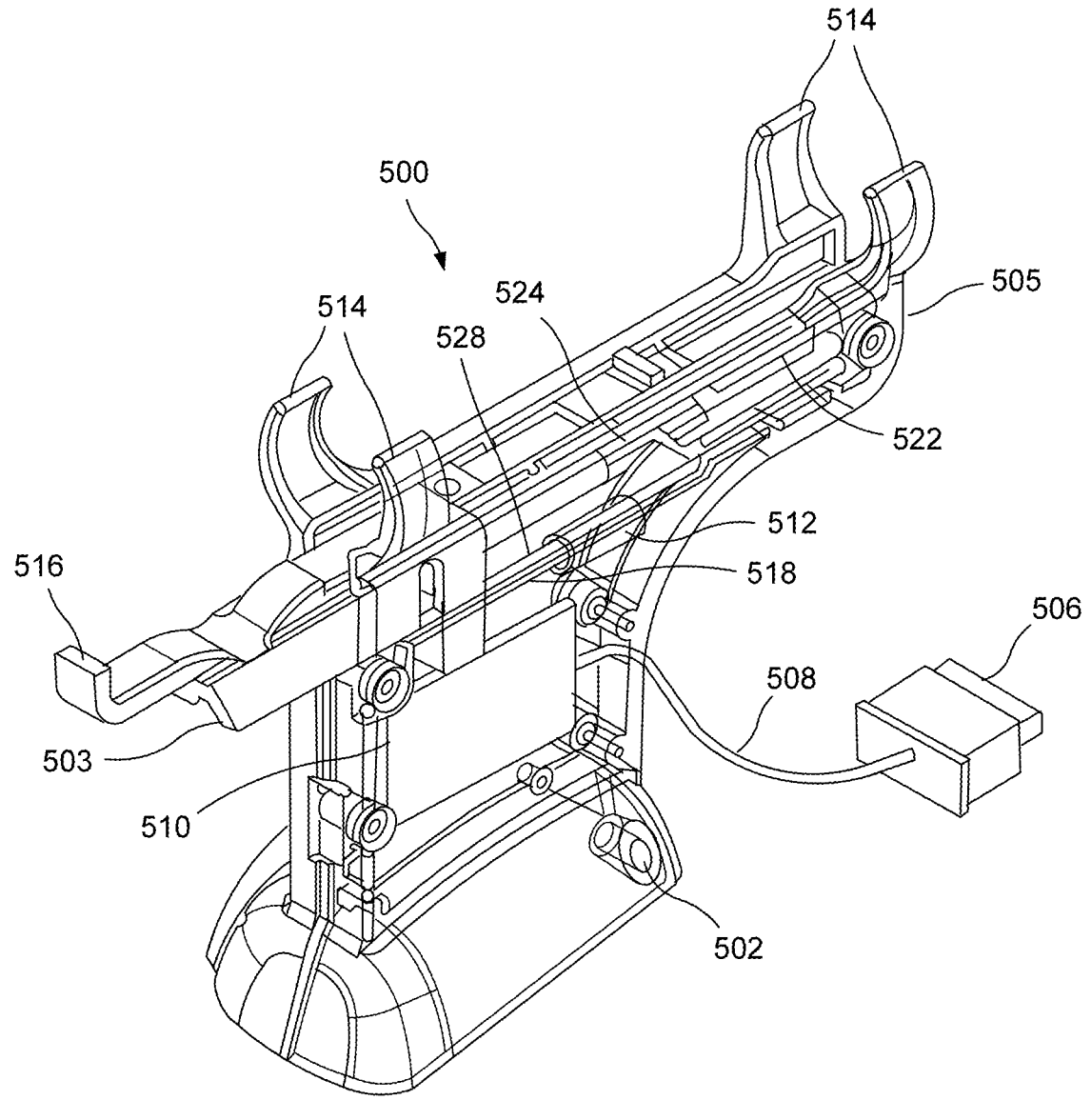
F I G. 5B

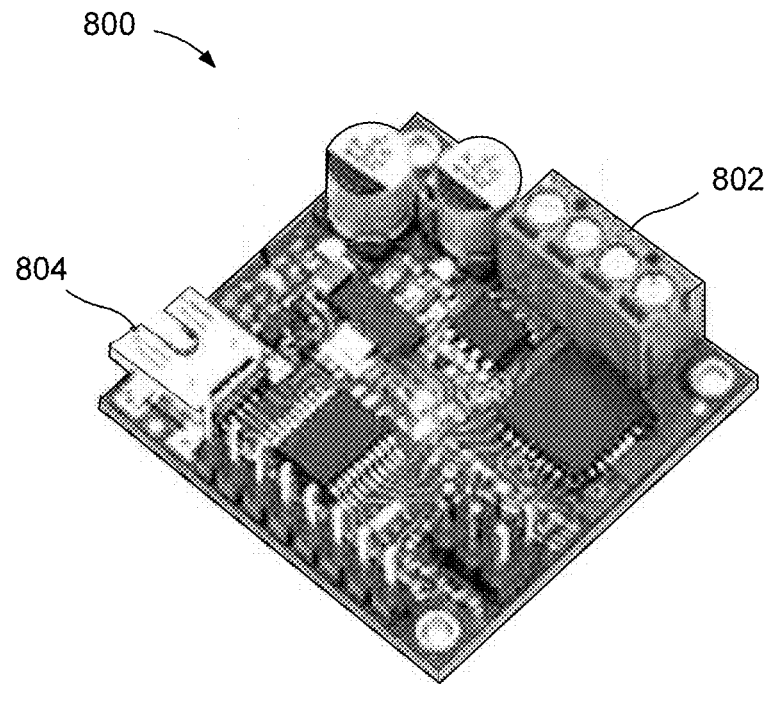
F I G. 8
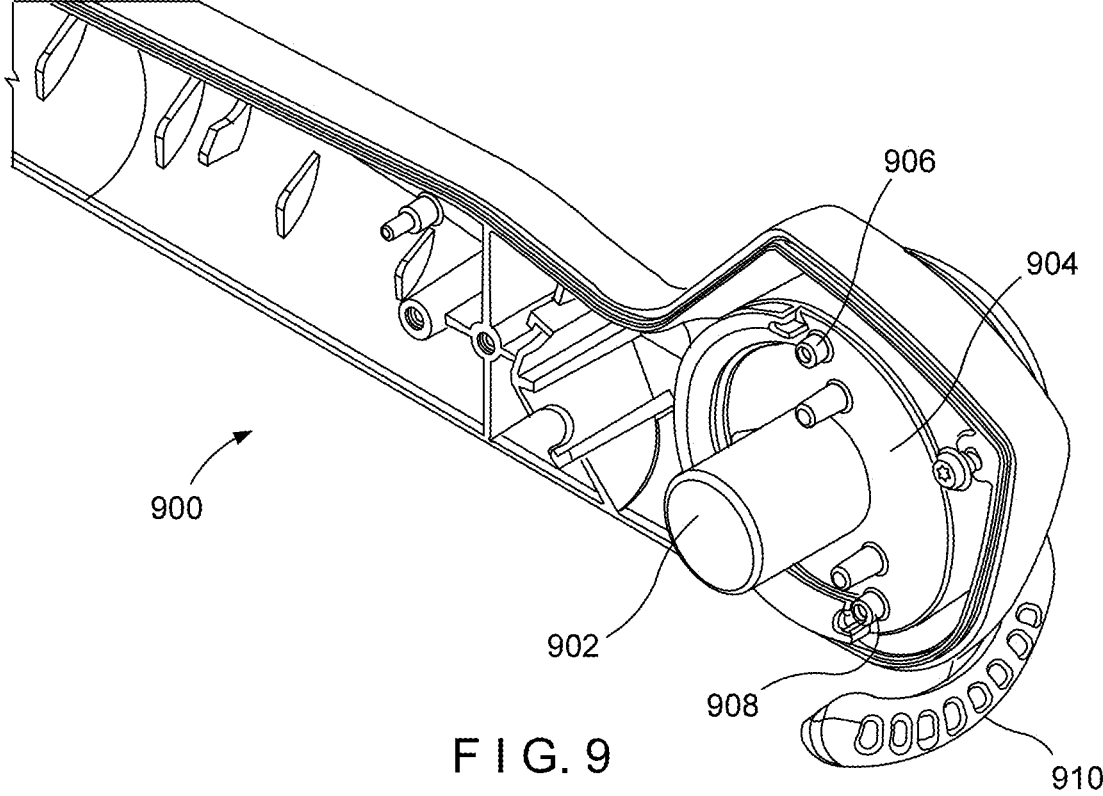
F I G. 9

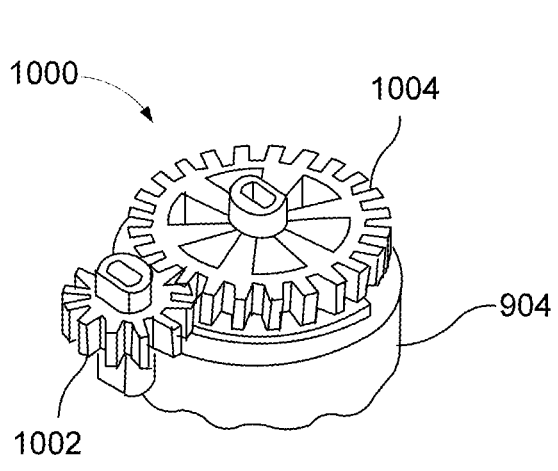
F I G. 10A
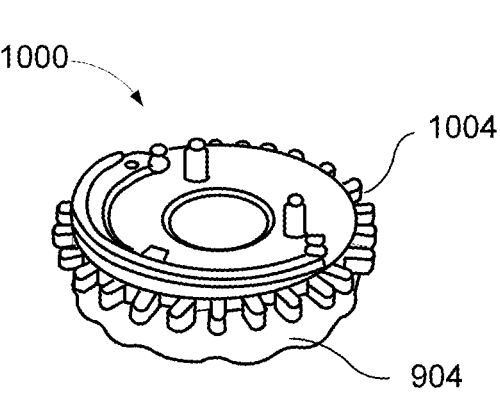
F I G. 10B
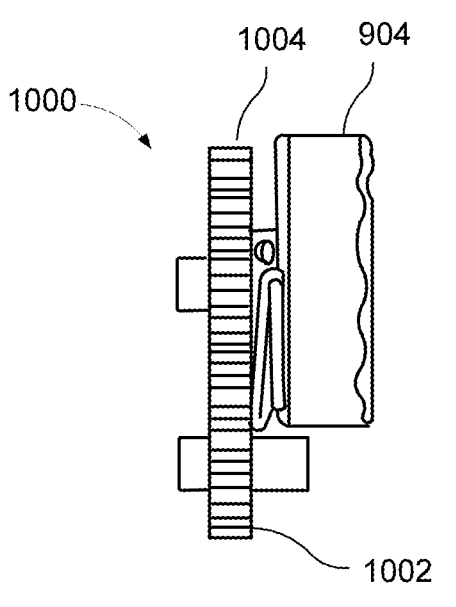
F I G. 10C
F I G. 10D 1100
1102
1106
904
1104
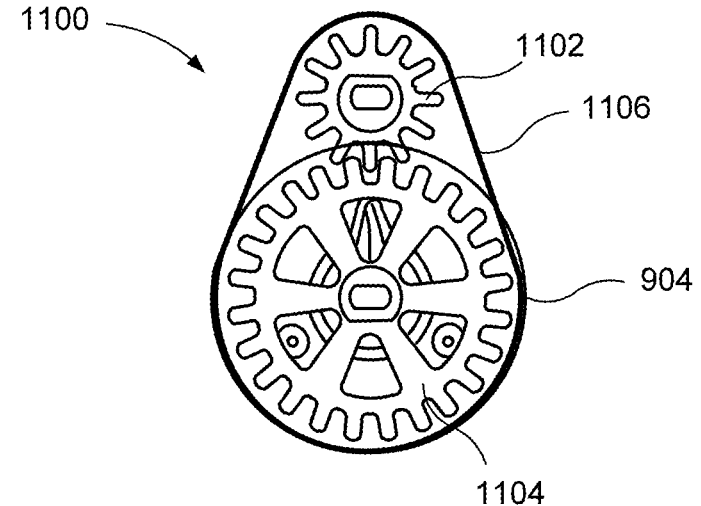
F I G. 11
1200
1201
1203
1204    1202
1205
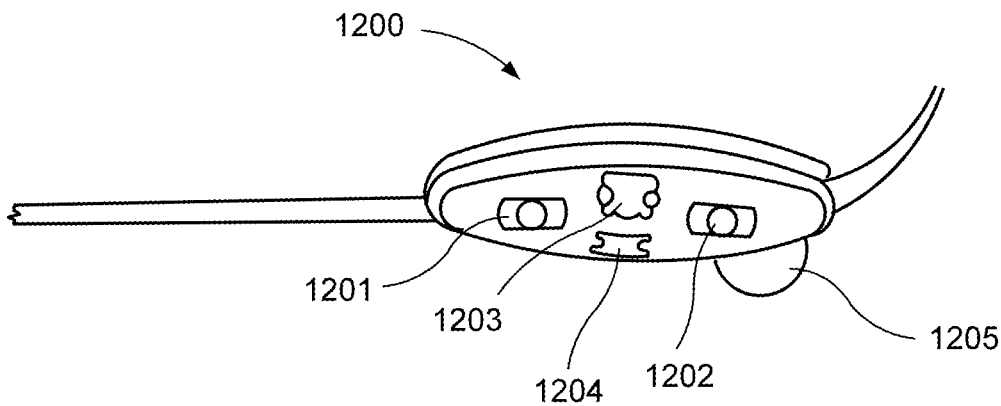
F I G. 12

ENDOSCOPIC DEVICE WITH USB PORT AND POWERED ACCESSORIES

PRIORITY CLAIM

This application is a continuation of U.S. application Ser. No. 16/948,027, filed on Aug. 27, 2020, which claims priority to U.S. Provisional Application No. 62/904,909, filed on Sep. 24, 2019; the disclosure of each of which is incorporated herein by reference.

FIELD

The present disclosure relates to an endoscopic device and, in particular, an endoscope handle with USB port and powered accessories.

BACKGROUND

Various accessory devices may be used with an endoscopic device to perform various diagnostic and treatment procedures in the imaged cavity. However, the accessory devices may not always be compatible with the endoscopic device. For example, the physical configurations of the devices may be difficult to use in conjunction, or the devices may not be programmatically compatible.

SUMMARY

The present disclosure relates to an endoscopic deployment device which includes a body mountable on an endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through a working channel of an endoscopic shaft of the endoscopic device, the body having a carrier channel sized for the carrier to slide therein, wherein the end effecter is actuatable between an extended open position and a retracted closed position by sliding the carrier in the carrier channel which in turn slides the outer sheath over the end effector shaft to uncover or cover the end effector; a communication interface extending from the body and configured to be mated with a corresponding communication interface on the endoscopic device on which the body is mounted to receive power therefrom and exchange data therewith; and a motor having a drive shaft coupled to the carrier, rotation of the drive shaft sliding the carrier in the carrier channel and actuating the end effector in response to a signal.

In an embodiment, the signal is generated based on actuation of an actuator on the endoscopic device.

In an embodiment, the actuator is a button pad controlling the motor via the mated communication interfaces of the endoscopic deployment device and the endoscopic device.

In an embodiment, the signal is generated in response to an endoscopic sensor reading.

In an embodiment, the motor is a stepper motor.

In an embodiment, the drive shaft has an arm extending orthogonally therefrom coupled to a slot in the carrier and the arm has a pin at an end of the arm opposite the drive shaft, the pin being coupled to the slot so that, when the drive shaft rotates, the pin slides in the slot in a direction orthogonal to the carrier channel and the carrier slides in the carrier channel.

In an embodiment, the drive shaft is a lead screw coupled to a threaded through-hole extending through a portion of the carrier parallel to the carrier channel so that, when the drive shaft rotates, the carrier slides in the carrier channel.

In an embodiment, a pinion gear is coupled to the drive shaft and to a rack that is an integral portion of the carrier so that, when the drive shaft rotates, the pinion gear drive the rack and the carrier slides in the carrier channel.

In an embodiment, the end effector device is a retrieval device for capturing objects at a distal end of the endoscopic shaft.

In an embodiment, the end effector device is a laser fiber or energy fiber for fragmenting or cauterizing objects at a distal end of the endoscopic shaft.

In an embodiment, the end effector device has a Segura™ handle for coupling to the carrier of the endoscopic deployment device, wherein the carrier and a slide of the Segura™ handle are positioned fully proximally prior to attaching the Segura™ handle to the endoscopic deployment device.

In an embodiment, the endoscopic device has a proximal communication interface and a distal communication interface and the communication interface of the endoscopic deployment device is compatible with the proximal communication interface of the endoscopic device.

In addition, the present disclosure relates to an endoscopic device which includes an elongated flexible endoscopic shaft including a working channel and a deflectable distal tip, the flexible endoscopic shaft being sized and shaped for insertion to a target site within a living body, the distal tip including a camera; a handle from which the endoscopic shaft extends distally, the handle including a pull wire wheel comprising pull wire attachments from which first and second pull wires extend distally through the endoscopic shaft to the distal tip, rotation of the pull wire wheel deflecting the distal tip by tensioning a first one of the first and second pull wires and slacking a second one of the first and second pull wires, the handle including an actuator, a proximal end of the handle including a communication interface for connecting an accessory device; and a motor including a rotatable drive shaft coupled to and configured to rotate the pull wire wheel in response to a signal.

In an embodiment, the deflection knob operates as a switch so that deflecting the deflection knob in a first direction rotates the pull wire wheel a predefined angular extent to apply tension to the first one of the first and second pull wires and deflecting the deflection knob in a second direction rotates the pull wire wheel a predefined angular extent to apply tension to the second one of the first and second pull wires.

In an embodiment, the signal is generated by a button pad on an exterior of the handle.

Furthermore, the present invention relates to a method which includes attaching an endoscopic deployment device to an endoscopic device, the endoscopic deployment device comprising a body mountable on the endoscopic device, the body having a movable carrier couplable to an elongated end effector device, the elongated end effector device having an end effector shaft covered by an outer sheath and an end effector extending from a distal end of the end effector shaft, the outer sheath being sized and shaped for insertion through a working channel of an endoscopic shaft of the endoscopic device, the body having a carrier channel sized for the carrier to slide therein, wherein the end effecter is actuatable between an extended open position and a retracted closed position by sliding the carrier in the carrier channel which in turn slides the outer sheath over the end effector shaft to uncover or cover the end effector, the endoscopic deployment device further comprising a communication interface extending from the body and configured to be mated with a corresponding communication interface on the endoscopic device on which the body is mounted to receive power therefrom and exchange data therewith, the endoscopic deployment device further comprising a motor having a drive shaft coupled to the carrier; and actuating the motor in response to a signal, the actuation of the motor rotating the drive shaft and sliding the carrier in the carrier channel to actuate the end effector.

In an embodiment, the actuator is a button pad on the endoscopic device, the button pad being operated with a thumb of a grip hand of a user.

In an embodiment, the button pad further actuates a deflection of a distal end of the endoscopic shaft.

In an embodiment, the motor is a stepper motor.

In an embodiment, the end effector device is a retrieval device for capturing objects at a distal end of the endoscopic shaft.

BRIEF DESCRIPTION

FIG. 4A shows a transparent side view of a first embodiment of a motorized deployment device.

FIG. 4B shows a transparent perspective view of the motorized deployment device of FIG. 4A.

FIG. 5A shows a transparent side view of a second embodiment of a motorized deployment device.

FIG. 5B shows a transparent perspective view of the motorized deployment device of FIG. 5A.

FIG. 8 shows a stepper motor control board.

FIG. 9 shows a handle of an endoscopic device with a motor for controlling the deflection of a distal tip.

Figure 1A:
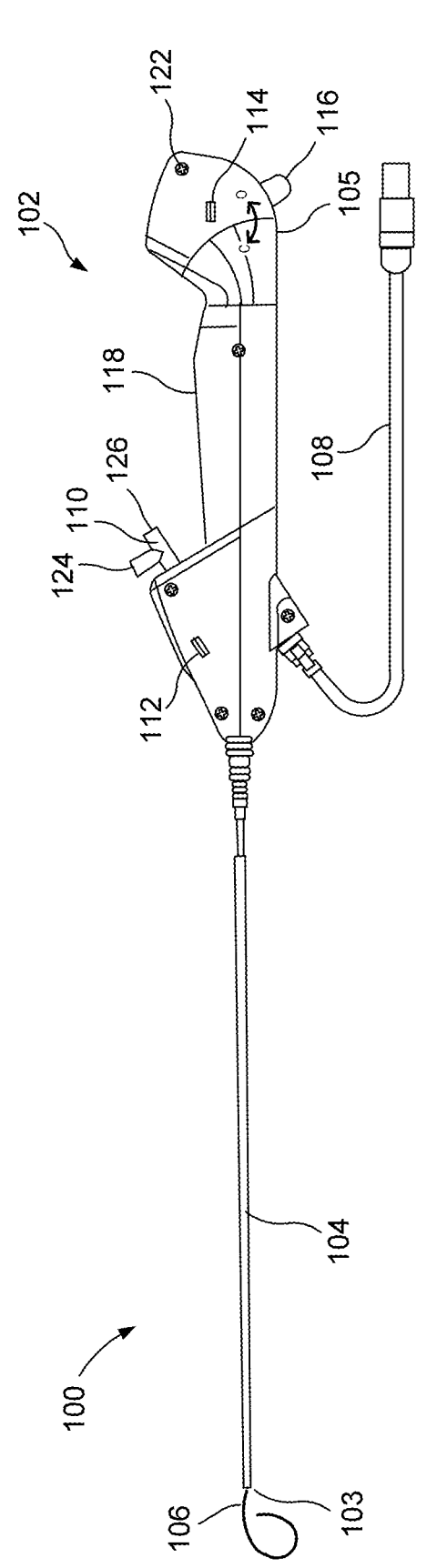
FIG. 1A shows a front view of an endoscopic device compatible with powered accessories according to various exemplary embodiments of the present disclosure.

FIGS. 10A-C show a gear train for driving a pull wire wheel of the device of FIG. 9.

FIG. 10D shows the pull wire wheel of the device of FIG. 9 fashioned with a gear.

FIG. 11 shows the gear train of FIGS. 10A-C with a pulley.

FIG. 12 shows an ergonomic button pad for controlling a scope tip and an elongated end effector device.

DETAILED DESCRIPTION

The present disclosure may be further understood with reference to the following description and the appended drawings, wherein like elements are referred to with the same reference numerals. The exemplary embodiments describe an endoscope having a scope handle with one or more external communication interfaces (e.g., USB ports) and accessory devices compatible with the endoscope and pluggable thereinto. For example, the accessory devices may include a pressure sensor, a temperature sensor, a flow sensor, an additional camera, an additional light, an optical sensor, a catheter, a laser time-of-flight distance sensor, a deployment device, other sensors or combinations thereof.

In another embodiment, an accessory device is described that is a motorized deployment device for controlling an elongated end effector device to capture e.g. kidney stones or the like. The motorized deployment device is compatible with the endoscope or may be integrated with the endoscope in a monolithic handle. The elongated end effector device refers to any one of a number of devices compatible with and actuated by the motorized deployment device. For example, the elongated end effector device may be the retrieval device for capturing kidney stones, a laser fiber device, a therapy needle, snares, forceps, band ligation devices, etc. Any of the elongated end effector devices may be fitted with, for example, a Segura™ or Dakota™ handle sized and shaped to be used with the motorized deployment device. Thus, any elongated end effector device compatible with and fitted with a Segura™/Dakota™ handle (or a similar device) may also be used with the motorized deployment device.

In still another embodiment, the endoscope handle has an motor for controlling the articulation of the distal tip of the endoscopic shaft. The motor may be, e.g., a stepper motor allowing for precise positioning and holding of the shaft tip and/or precise control of the end effector feature of the elongated device. The motor may be internal to the handle or may be externally coupled to the handle, e.g., connected to a pull wire wheel by a flexible drive shaft extension or the like.

In each of the embodiments, the communication interfaces between the scope handle and the accessory device(s), whether internal or via external communication interfaces, are arranged so that an operating physician may operate the articulation of the distal shaft tip and control the accessory device in an ergonomic manner. For example, in one embodiment, where the motorized deployment device is connected to the scope handle via an external communication interface, the deflection knob for the distal shaft tip and the button control for the motorized deployment device are arranged so that both may be operated simultaneously or independently without overstressing the physician's hand.

In another embodiment, where the motorized deployment device is monolithic with or otherwise compatible with the scope handle, a button pad may be used to operate both the shaft tip and the elongated device. The button pad may include, for example, four momentary buttons located on the bottom side of the scope handle and may be operated by the physician's grip hand thumb. Depressing a button causes a movement to occur to the scope shaft or the end effector, and releasing the button causes the stepper motor to stop and hold the current position. In another embodiment, a non-momentary button may be used such as a typical on/off switch. In still another embodiment, control is fully implemented remotely from the devices via, e.g., a console.

The present embodiments have a data bus in the scope handle where data may be received via the various accessory devices and control for the devices may be implemented. The handle may be coupled to an endoscopic console or the like via a cable, with data from the devices being sent thereto or control of the devices being implemented therefrom. In some embodiments, data from one of the accessory devices and/or the endoscope may be used to control the operation of another one of the accessory devices and/or the endoscope. For example, a reading from a pressure sensor may trigger an operation of an irrigation mechanism. In another example the output from a laser-distance sensor may adjust/optimize the distance from a laser fiber tip to a ureteral stone via the stepper motor to maximize laser efficiency during stone fragmentation. In another embodiment the data from an accessory device is displayed on e.g. a monitor screen for the physician to evaluate and react accordingly.

Figure 1B:
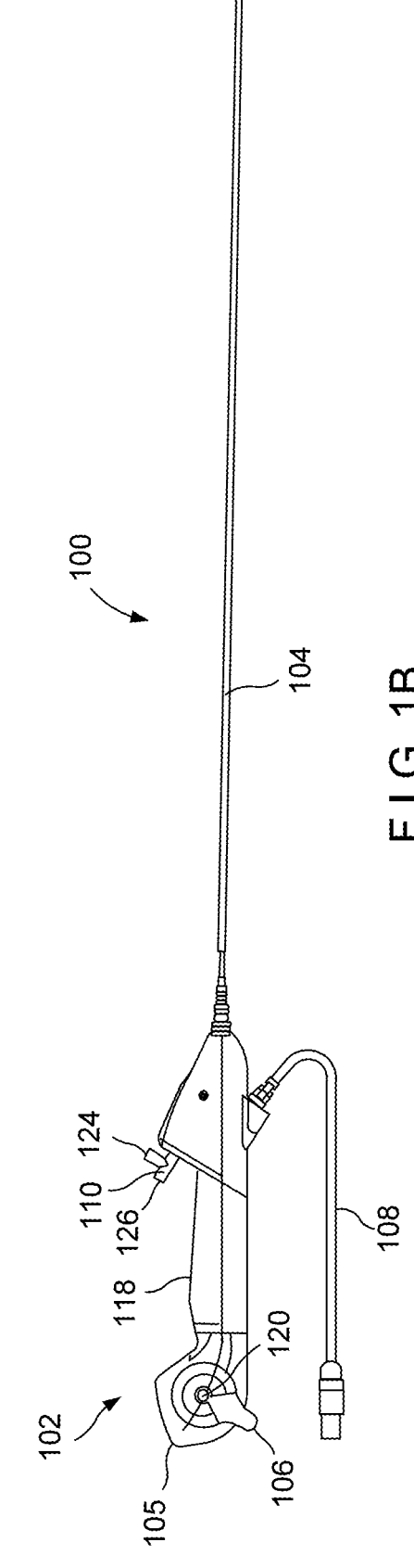
FIG. 1B shows a rear view of the endoscopic device of FIG. 1A.

FIGS. 1A-1B show a front view and a rear view of an endoscopic device 100 compatible with powered and data accessories according to various exemplary embodiments of the present disclosure. The endoscopic device 100 may be specific to a particular endoscopic procedure, such as, e.g., ureteroscopy, or may be a general-purpose device suitable for a wide variety of procedures. The device 100 includes a handle 102 connected to an endoscopic shaft 104 with a deflecting distal tip 106 at a distal end 103. The distal tip 106 has a camera and may, for example, have full 270° deflection capabilities in more than one direction for viewing patient anatomy as would be understood by those skilled in the art.

The handle 102 of the endoscopic device 100 has a plurality of elements configured to facilitate the endoscopic procedure. A cable 108 extends from the handle 102 and is configured for attachment to an electronic device (not pictured) such as e.g. a computer system, a console, a microcontroller, etc. for providing power, analyzing endoscopic data, controlling the endoscopic intervention, or performing other functions. The electronic device to which the cable 108 is connected may have functionality for recognizing and exchanging data with other endoscopic accessories, to be described in detail below. The handle 102 has a grip area 118 for the operating physician to grasp while performing the endoscopic procedure. A deflection knob 116 at a proximal end 105 of the device may be actuated to control the deflection of the distal tip 106 as would be understood by those skilled in the art. Even when an endoscope has a motorized deflection means, to be described in detail below, a short handle version of the deflection knob 116 is present, in this embodiment, for manually straightening the distal tip 106 and removing the shaft 104 from the patient anatomy in case of e.g. power failure.

The handle 102 further has at least one communication interface for attaching accessory devices. In the present embodiment, the handle 102 has a first communication interface 112 and second communication interface 114 that are, in this embodiment, Universal Serial Bus type-C (USB-C) ports. However, more or less communication interface of various types, including, for example, custom interfaces, may be used. In other embodiments, the handle 102 has only one communication interface but may receive e.g. a USB hub with multiple ports for connecting multiple accessories. The communication interfaces 112, 114 may provide power to the accessory devices in addition to exchanging data therewith. Thus, the accessory devices need not have separate cables running to the console or a battery that adds additional weigh to the handle 102. The accessory device may be uniquely associated with the device 100 and recognized by the console through "plug and play" functionality without any user setup required.

A T-connector 110 extends from a distal portion of the handle 102 and provides two ports 124, 126 for accessing the working channel of the endoscopic shaft 104. In this embodiment, the first and second ports 124, 126 are arranged perpendicularly to one another with the first port 124 facing distally and the second port 126 facing proximally. An accessory device or an elongated end effector device may be passed through either one of the first and second ports 124, 126, however, the second port 126 may be preferred when the device is proximal to the T-connector 110. In another embodiment, a Y-connector is used with first and second ports both facing proximally, such that two devices may be passed into the working channel of the endoscopic shaft 104 from a position proximal to the Y-connector.

Various accessory devices may be mated with either of the two communication interfaces 112, 114, however, certain of the accessory devices are more compatible with either one of the two interfaces 112, 114. The first communication interface 112 is located distally on the handle 102. Certain of the accessory devices have corresponding communication interfaces, e.g., male USB-C ports, extending from the devices that lend themselves to spatial compatibility with the first communication interface 112.

Figures 2, 3:
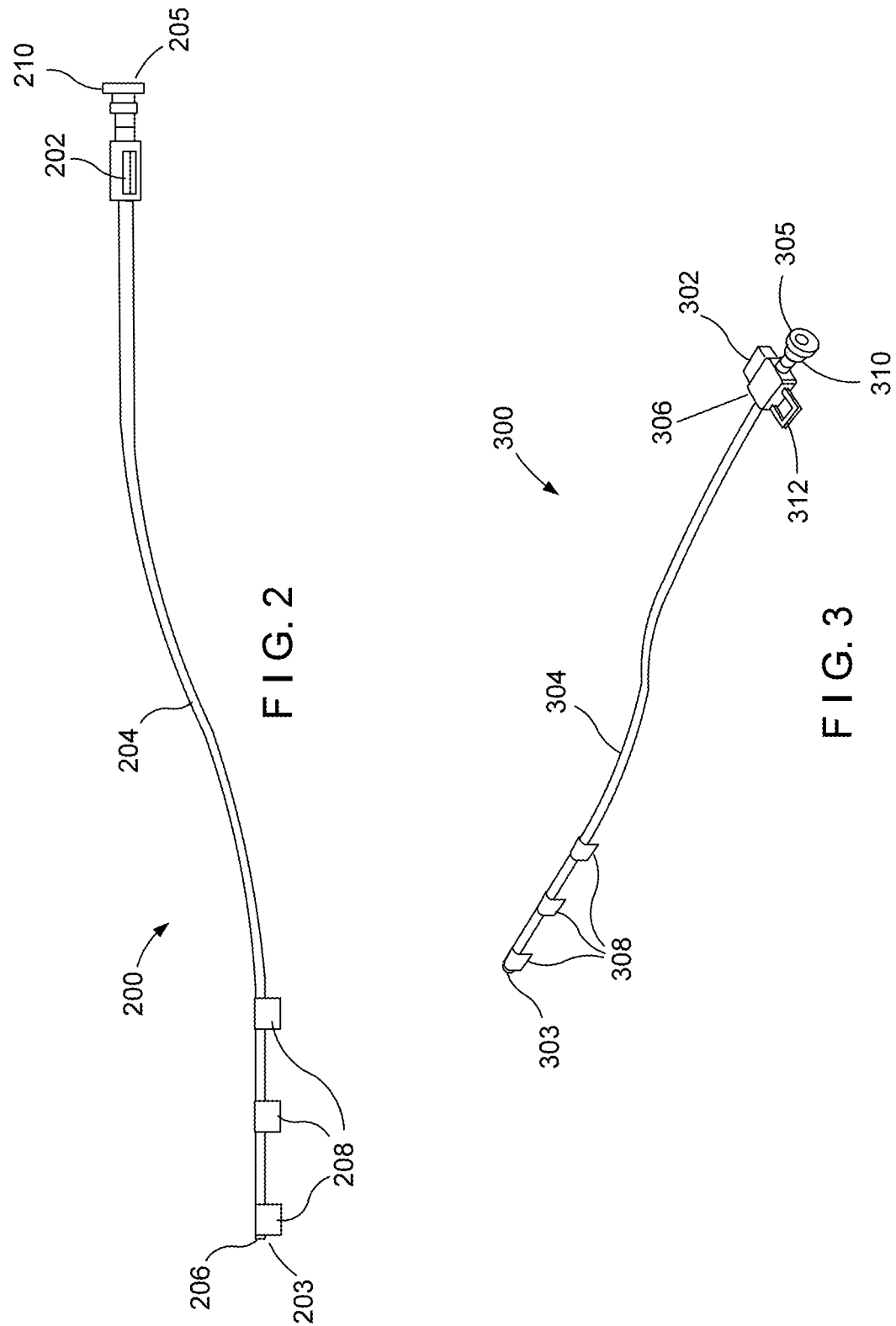
FIG. 2 shows a pressure sensor device configured for compatibility with the endoscopic device of FIG. 1A.
FIG. 3 shows a flow sensor device configured for compatibility with the endoscopic device of FIG. 1A.

For example, FIG. 2 shows a pressure sensor device 200 configured for compatibility with the endoscopic device 100, particularly with the first communication interface 112 of the endoscopic device 100. The pressure sensor device 200 has a communication interface 202 that may be mated with, e.g., inserted into, the first communication interface 112 of the endoscopic device 100. The pressure sensor device 200 has a shaft 204 extending from a proximal end 205 of the device 200 to a distal end 203 of the device 200. The shaft 204 has a through-lumen, i.e., channel, extending through its length. The proximal end of the shaft 204 has a female Luer hub 210 extending therefrom and the communication interface 202 adjacent thereto. The communication interface 112 of the endoscopic device 100 is angled so that when the pressure sensor device 200 is attached to the endoscopic device 100, the Luer hub 210 is oriented in a manner similar to the second port 126 of the T-connector 110. Thus, the pressure sensor device 200 is more easily coupled with a male Luer port for e.g. fluid communication during use.

The pressure sensor device 200 has a pressure sensor 206 at a distal end of the shaft 204 and a plurality of clips 208 adjacent thereto for securing the shaft 204 of the pressure sensor device 200 to the endoscopic shaft 104. Although the present embodiment uses the clips 208, the shaft 204 may be secured to the endoscopic shaft 104 by other means such as, e.g., holders or the like.

As noted above, the pressure sensor device 200 may also be mated with the second communication interface 114 of the endoscopic device 100. However, in the presently described embodiment, mating with the first communication interface 112 is preferable in view of the ease with which the shaft 204 of the pressure sensor device 200 may be clipped to the shaft 104 of the endoscopic device 100 as well as the positioning of the medical luer hub 210.

In another example, FIG. 3 shows a flow sensor device 300 configured for compatibility with the endoscopic device 100, particularly with the first communication interface 112 of the endoscopic device. Similar to the pressure sensor device 200, the flow sensor device 300 has a communication interface 302 that may be mated with the first communication interface 112 of the endoscopic device 100. The flow sensor device 300 has a shaft 304 extending from a proximal end 305 of the device 300 to a distal end 303 of the device 300. The shaft 304 has a through-lumen extending through its length. The proximal end of the shaft 304 has a female Luer hub 310 extending therefrom, the communication interface 302 adjacent thereto and a handle 312. Similar to the pressure sensor device 200, the flow sensor device 300 is easily coupled with a male Luer port for fluid communication or any other reason.

The flow sensor device 300 has a flow sensor 306 adjacent to the handle 312 and a plurality of clips 308 adjacent to a distal end of the shaft 304 for securing the shaft 304 of the flow sensor device 300 to the endoscopic shaft 104. Similar to the pressure sensor device 200, the flow sensor device 300 may use attachment means other than the clips 308 such as, e.g. holders or the like. The pressure sensor device 200 may also be mated with the second communication interface 114 of the endoscopic device 100, however, mating with the first communication interface 112 is preferable in view of the spatial benefits discussed above.

The second communication interface 114 is positioned proximally on the handle 102 and is compatible with accessory devices configured for insertion through a working channel of the endoscopic shaft 104 via, for example, the second port 126. For example, an accessory device such as an additional camera, an additional light, an optical sensor, or other device may be mated with the second communication interface 114 and inserted into the working channel. In this way, the cables/shafts of the devices are out of the way of the operating physician and can be used without significant bending of the accessory.

However, these devices may also have a flexible cable that is inserted into the first communication interface 112 and flexed into the working channel without damaging the cable. Because the second communication interface 114 is proximal to the T-connector 110, with the second port 126 of the T-connector 110 directed proximally, there may be instances where a fluid being used during a ureteroscopic procedure leaks and/or splashes proximally. Thus, the proximal second communication interface 114 may have a fluid seal such as a Tuohy borst adapter, a UroLok™ or a Gateway™. The console cable 108 of the endoscopic device 100 may be associated with one of the communication interfaces 112, 114 such that an interface on the handle 102 is not necessary. For example, the cable 108 may be bifurcated and have an interface, e.g., USB port, extending from the bifurcated part of the cable 108.

The handle 102 of the endoscopic device 100 in the present embodiment has two mount holes 120, 122 positioned to couple to, for example, a motorized deployment device 400 compatible with an elongated end effector device. The elongated end effector device may be any one of a number of devices having a variety of purposes such as, e.g., capturing and removing objects such as kidney stones, to be explained in further detail below.

FIG. 4A shows a transparent side view and FIG. 4B shows a transparent perspective view of the motorized deployment device 400. The motorized deployment device 400 may be coupled to the endoscopic device 100 at the mount holes 120, 122 with corresponding mount pins 402, 404. The deployment device 400 has a communication interface 406 that may be mated with, e.g., inserted into, the second communication interface 114 of the endoscopic device 100. The communication interface 406 may be, e.g., a male USB-C port. The communication interface 406 is connected via a flexible cable 408 to a control board 410 for a motor 412. The control board 410 includes an electrical port, in this case for connecting a USB, driver circuitry and motor terminals for connecting the motor 412. The motor 412 may be, e.g., a stepper motor.

The motor 412 may be actuated by a signal provided by e.g. the button pad 1200 shown in FIG. 12. In another embodiment, the signal is generated in response to an endoscopic sensor reading. If the flexible cable 408 is sufficiently long the communication interface 406 may be mated with the first communication interface 112 of the endoscopic device 100, however, in the presently described embodiment, the motorized deployment device 400 is particularly suited for connection via the second communication interface 114. The connection to the deployment device 400 via one of the communication interfaces 112, 114 allows for actuation of the deployment device 400 via controls on the handle 102.

The motorized deployment device 400 has a handle coupler 414 extending from a distal end 403 of the device 400 to a proximal end 405 of the device 400. The handle coupler 414 is configured to receive a handle of the elongated end effector device, to be described below with respect to FIGS. 6-7. The elongated end effector device comprises a pull wire and an outer sheath to be fed through the working channel of the shaft 104 via the T-connector 110 of the endoscopic device 100 or other embodiments of the endoscopic device. The elongated end effector device includes a handle at the proximal end and an end effector at the distal end of the pull wire, the end effector being actuatable by a slide on the handle between an extended open and a retracted closed state for, for example, grasping objects or extending/retracting a laser fiber or a therapy needle during the endoscopic procedure.

In an alternate embodiment, the elongated end effector device and the motorized deployment device 400 are fashioned in a single monolithic unit. The end effector is actuatable via linear motion of a carrier 416 coupled to the slide of the elongated end effector device handle, to be described in detail below. For example, when the elongated device handle is inserted into the handle coupler 414, distal movement of the carrier 416 may cause the slide of the elongated end effector device to close the end effector, while proximal movement of the carrier 416 may cause the end effector to open. The motion of the carrier 416 is implemented via the motor 412 via an actuation linkage internal to the deployment device 400, to be described below.

The carrier 416 of the deployment device 400 is configured to slide within a channel 424 of the device 400. The channel 424 prevents any movement other than the proximal/distal sliding. The carrier 416 has a slot 422 where a pin 420 is configured to slide, the pin 420 being connected to the motor 412 via an arm 418. When the motor 412 is actuated the arm 418 is caused to rotate about a predefined arc 426. The linkage of the pin 420 with the slot 422 translates the angular motion of the arm 418 into linear motion of the carrier 416. The slot 422 allows the pin 420 to translate slightly in a direction orthogonal to the proximal/distal direction while driving the carrier 416 in the proximal/distal direction. When the carrier 416 is brought to its most distal position the end effector is fully closed, and when the carrier 416 is brought to its most proximal position the end effector is fully open, with varying degrees of openness/closedness between its most distal and most proximal positions.

In an alternate embodiment, as shown in FIGS. 5A-5B, a deployment device 500 extends from a distal end 503 to a proximal end 505 and may drive a carrier 516 using a lead screw in lieu of the linkage described with respect to the deployment device 500. Similar to the first deployment device 400, the second deployment device 500 has mount pins 502, 504 for attaching the second deployment device 500 to the endoscopic device 100. Additionally, a communication interface 506, a flexible cable 508, a driver and control board 510, a handle coupler 514, the carrier 516 and a channel 528 are substantially similar to those described with respect to the deployment device 400. However, the deployment device 500 has two location options for a motor, both of which are coupled to lead screws, i.e. screws used as a linkage to translate rotational motion into linear motion.

In a first embodiment, a motor 512 is disposed at a location adjacent to and oriented parallel to the channel 528 housing the carrier 516. When the motor 512 is actuated, a lead screw 518 extending from the motor is rotated. The lead screw 518 is coupled to a threaded through-hole 520 extending through a portion of the carrier 516. Thus, as the lead screw 518 is rotated, the carrier 516 is driven in a proximal/distal direction. In a second embodiment, a motor 522 is disposed at a location proximal to the channel 528 housing the carrier 516. A lead screw 524 extends from the motor 522 and is coupled to a threaded through-hole 526 extending through a proximal portion of the carrier 516. The second motor 522 drives the carrier 516 in a substantially similar manner as the first motor 512.

In an alternate embodiment, the devices 400, 500 may implement a rack and pinion mechanism to drive the linear motion of the carrier 416, 516. A pinion gear may be attached to the stepper motor shaft and the rack may be an integral portion of the carrier.

Figure 6:
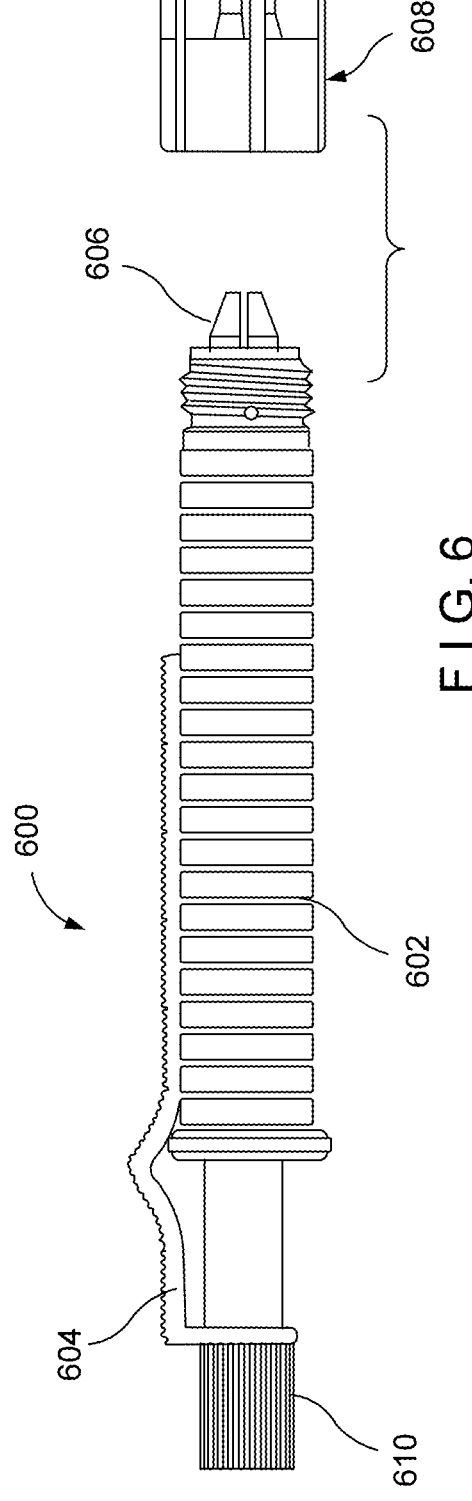
FIG. 6 shows an exemplary Segura™ handle compatible with the motorized deployment devices of FIGS. 4A-5B and an elongated end effector device.
Figure 7C:
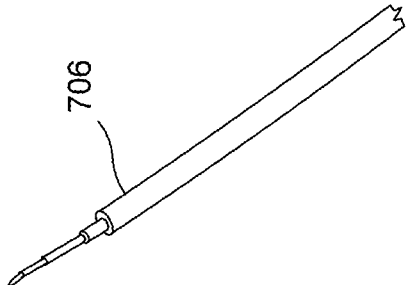
FIGS. 7A-7F show exemplary elongated end effector devices compatible with a Segura™/Dakota™ handle.
Figure 7F:
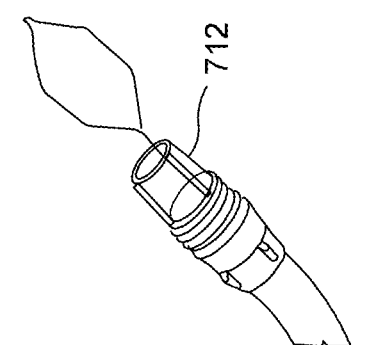
Figure 7B:
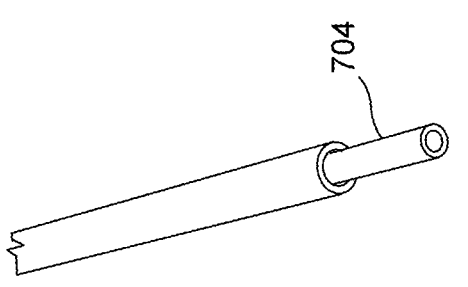
Figure 7E:
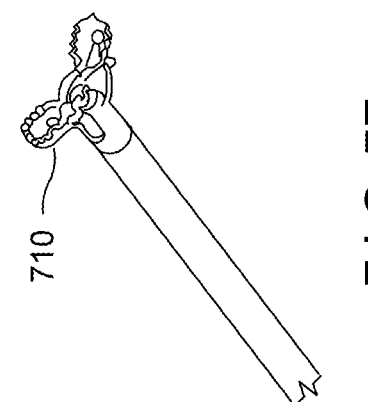
Figure 7A:
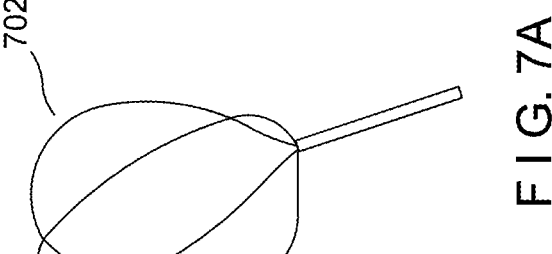
Figure 7D:
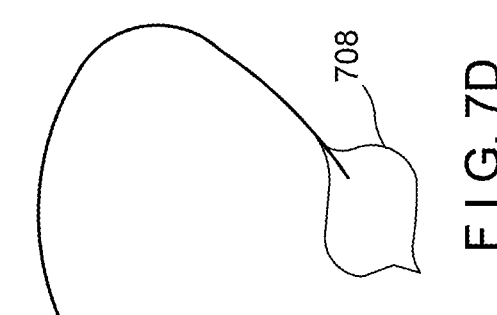

FIG. 6 shows an exemplary Segura™ handle 600 that may be fitted to any of the aforementioned elongated end effector devices. In another embodiment, a Dakota™ handle may be used, which is similar to the Segura™ handle but is modified to have a sure open trigger. Thus, the handle 600 may be either of a Segura™ or a Dakota™ handle, depending on the elongated end effector device to which it is fitted, or may be a similar device for actuating an end effector device.

The Segura™ handle 600 has a body 602 over which a slide 604 may slide. A male luer 610 is attached to a distal end of the slide 604, while a shaft, i.e. pull wire of the elongated end effector device is held by a jaw vise 606 at a proximal end 605 of the body 602. A cap 608 forces the jaws 606 closed around the shaft of the end effector device as the cap 608 is screwed onto the body 602. The body 602 has a through-lumen (not pictured) for the shaft of the elongated end effector device. Thus, it may be seen that the slide 604 may move relative to the body 602 and the shaft of the elongated end effector device.

An outer sheath of the end effector device is connected vis a female luer to the male luer 610 and extends to cover the end effector at the distal end of the end effector device. When the slide 604 is moved distally it in turn moves the outer sheath distally over the end effector to close the end effector, and when the slide 604 is moved proximally it in turn moves the outer sheath proximally to uncover the distal end of the end effector, causing the self-opening, memory set end effector to open. A stroke-limiter in the Segura™ handle 600 governs the travel of the slide 604 relative to the end effector size, where T is the travel length of the slide 604.

As discussed previously, the carriers 416, 516 of the deployment devices 400, 500 are, in these embodiments, sized and shaped for compatibility with the slide 604 of the Segura™/Dakota™ handle 600. Thus, when the deployment device 400 is actuated to move the carrier 416 in a proximal or distal direction, the slide 604 is correspondingly moved with respect to the body 602 and the end effector of the end effector device is moved towards open or moved towards closed.

FIG. 7 shows examples of elongated end effector devices compatible with the Segura™/Dakota™ handle 600, including a stone/particle retrieval basket. FIGS. 7A-7F show a Zero Tip™ retrieval basket 702, a laser fiber device 704, a therapy needle 706, a snare 708, forceps 710 and a band ligator 712, respectively. Each of the elongated end effector devices may be fitted with a Segura™/Dakota™ handle and may be operated by the deployment device 400 or 500.

The motors described with respect to deployment devices 400 and 500 may be, e.g., a DC motor, a Servo motor, a stepper motor, or the like. The preferred embodiment for the motor is the stepper motor. A stepper motor is a brushless electromechanical device that converts the train of electric pulses applied at their excitation windings into precisely defined step-by-step mechanical shaft rotation. The shaft of the motor rotates through a fixed angle for each discrete pulse, which may be translated to linear motion in any of the aforementioned ways. Each pulse provides one step of motion, i.e., the angle through which the stepper motor shaft turns for each pulse is referred to as the step angle, generally expressed in degrees.

The position of motor shaft is controlled by controlling the number of pulses. This feature makes the stepper motor to be well suited for an open-loop control system wherein the precise position of the shaft is maintained with an exact number of pulses without using a feedback sensor. If the step angle is smaller, the greater will be the number of steps per revolution and the higher will be the accuracy of the position obtained. The step angles can be as large as 90 degrees and as small as 0.72 degrees, however, the commonly used step angles are 1.8 degrees, 2.5 degrees, 7.5 degrees and 15 degrees.

The direction of the shaft rotation depends on the sequence of pulses applied to the stator. The speed of the shaft or the average motor speed is directly proportional to the frequency (the rate of input pulses) of input pulses being applied at excitation windings. Therefore, if the frequency is low, the stepper motor rotates in steps and for high frequency, it continuously rotates like a DC motor due to inertia. Stepper motors continue to generate holding torque even at standstill. This means that the motor can be held at a stopped position without using a mechanical brake. The built-in pulse generation function (controller) allows the stepper motor to be driven via a directly connected personal computer, programmable controller or console. The stepper motor may achieve precise positioning via digital control, such control to be explained in further detail below.

FIG. 8 shows a stepper motor control board 800. The control board 800 comprises a USB port 804 for connecting a USB cable and motor terminals 802 for connecting a stepper motor. The stepper motor control board 800 may be used in either of the deployment devices 400, 500 as the control boards 410 or 510 for motors 412, 512 or 522, when those motors are stepper motors. However, if a stepper motor is not used, the corresponding control board is configured to drive whichever motor is used. For example, if the motor 412 is a Servo motor, the control board 412 is a Servo motor control board. The motor control board may be custom built. The motor may be powered via the USB port 804, however, in another embodiment, the motor may be powered by batteries.

The deployment device 400 has buttons 430 for controlling the carrier movement via the control board 410 and motor 412. The deployment device 400 preferably has at least two buttons 430. For example, a first button may be depressed to advance the carrier in the distal direction and stop when the button is released. A second button may be depressed to advance the carrier in the proximal direction and stop when the button is released. A double tap of either button may bring the carrier to its most distal or most proximal position. Other button depression configurations may, for example, increase or decrease a speed of the carrier motion.

In the embodiment shown in FIG. 12, the most proximal button 1202 is for scope shaft up direction (US) and the most distal button 1201 is for scope shaft down direction (US). In other countries the proximal button is for down and the distal button is for up. The two side buttons 1203, 1204 on the button pad may be programmed by a user to either move the carrier distally or proximally when pressed since the microprocessor is executing the stepper motor's direction of movement via a program, when a conditional statement in the program is true. The up and down scope shaft buttons may also be switched by modifying a conditional statement without switching the pull wires of the pull wire wheel.

The placement of the buttons 430 adjacent to the grip area 118 and deflection knob 116 of the endoscopic device 100 (when the endoscopic device 100 and the deployment device 400 are attached) provides ergonomic benefits to the user of the devices. For example, a typical user may have difficulty operating a deployment device and scope deflection simultaneously, especially when the thumb is extended on the deflection knob 116 at full deflection, and especially if the user has a small hand. The spatial configuration of the devices 100, 400 allow for ease of use due to the proximity of the buttons 430 and deflection knob 116. The retrieval device 500 similarly has buttons 530 for controlling the carrier movement in a similar manner as that described above.

In an alternate embodiment, voice commands may be implemented for controlling the end effector, such as, but not limited to, "open," "close," "stop," "faster," "slower," "load," etc.

Different elongated end effector devices may be implemented in the deployment device 400, each one having a distinct data set for controlling the end effector. For example, each end effector device may have different stop limits or stroke lengths for the carrier. However, through the "plug-and-play" functionality of the endoscopic device 100, the data sets may be automatically loaded to the controller.

Alternately, a type of elongated end effector device may be selected through a drop-down menu on the console. To assemble the Segura™ handle to the deployment device 400 the carrier is moved to the most proximal position, e.g. by depressing the button 1203 of FIG. 12, and the slide of the Segura™ handle is also moved to the most proximal position. This would match the contours of the slide and carrier such that the Segura™ handle is aligned and can be snapped into the deployment device. Button 1204, for example, is depressed to close or retract the end effector before the end effector is inserted into the working channel of the scope. To remove the elongated end effector device the end effector is closed by depressing e.g. button 1204. The shaft of the end effector is withdrawn and the Segura™ handle can be unclipped from the deployment device and put aside for later use. Another elongated device can be quickly exchanged for the previous elongated device to perform its function In an alternate embodiment, the endoscopic device 100 and deployment devices 400 or 500 may be implemented in a single monolithic unit. In such an embodiment, instead of using mount holes and mount pins to connect the respective devices, the deployment device is built into the handle of the endoscopic device and all associated wiring is within the device.

In still another embodiment, the deflection of the distal tip 106 of the endoscopic device 100 may be motorized/wired using the same control board, such as the control board 800, as the deployment device 400. In such an embodiment, a second driver and a second motor would be implemented in the handle 102 for controlling the distal tip 106.

FIG. 9 shows a handle 900 of an endoscopic device with a motor 902 for controlling the deflection of a distal tip. The endoscopic device in this embodiment has two pull wires (not shown) for deflecting the distal tip in either of two directions. A pull wire wheel 904 has a first pull wire attachment 906 and a second pull wire attachment 908. The motor 902 is mounted in the handle 900 with its drive shaft mounted in the center of the pull wire wheel 904. A deflection knob 910 may be keyed to the rotation of the pull wire wheel 904 via a controller/driver and wiring (not shown). Thus, the deflection knob 910 may operate as a switch and rotate independently from the pull wire wheel 904.

When pressure is applied on the deflection knob 910 in a first direction the motor 902 will rotate the pull wire wheel 904 such that one of the two pull wires, e.g. the pull wire attached to the first pull wire attachment 906, pulls the distal tip of the endoscopic device in one of the two directions. Similarly, when pressure is applied on the deflection knob 910 in the second direction the motor 902 will rotate the pull wire wheel 904 such that the second of the two pull wires, e.g., the pull wire attached to the second pull wire attachment 908, pulls the distal tip of the endoscopic device in the second of the two directions. Release of the deflection knob 910 may stop the motor 902, allowing the position of the deflected distal tip to be maintained. The maximum angular travel of the motor 902 will be set to the limitations of the distal tip deflection.

A gear train may be used in the handle 900 in lieu of the motor 902 driving the pull wire wheel 904 directly. FIGS. 10A-C show a simple two gear train 1000 where a smaller gear 1002 drives a larger gear 1004 that rotates the pull wire wheel 904. The larger gear 1004 and the pull wire wheel 904 may be fashioned as a single part where the gear teeth extend from the circumference/perimeter of the pull wire wheel 904, as shown in FIG. 10D. FIG. 11 shows a two-gear train 1100 with a smaller gear 1102 and a larger gear 1104 comprising a pulley belt 1106. The mechanical advantage of the aforementioned embodiments is to use a less powerful/expensive motor. In the device 900, driving the pull wire wheel 904 directly will require a higher torque specification for the motor than would be needed using the gear train systems shown in FIGS. 10-11.

The aforementioned aspects of the present disclosure may be combined in various ways. In a first example, both the scope tip and the deployment device are motorized. FIG. 12 shows an ergonomic button pad 1200 for controlling the scope tip and the deployment device. The button pad 1200 has a first button 1201, a second button 1202, a third button 1203 and a fourth button 1204. The button pad 1200 is also adjacent to a shortened deflection knob 1205. The deflection knob 1205 is shortened to allow the placement of the button pad 1200 adjacent to the deflection knob 1205. In other embodiments, the deflection knob 1205 may be eliminated completely, with the deflection of the scope tip being controlled by the button pad 1200. In another embodiment, the shortened deflection knob may be used as a safety/bailout feature in case of e.g. power failure, considering the deflected scope shaft has to be straightened before it can be removed from the body without injuries.

The button pad 1200 is connected to a controller programmed for all aspects of the intervention. The button pad 1200 is located on the bottom side of the scope handle and may be operated, for example, by the thumb of the scope handle grip hand. For example, the first and second buttons 1201, 1202 (opposite one another) may be used to deflect the scope tip in either of the two directions. The third and fourth buttons 1203, 1204 (opposite one another) may be used to control the opening/closing of the elongated end effector device. A fifth button may be implemented, such that when the fifth button is "on," the third and fourth buttons 1203, 1204 are used to turn on/off the fluid management system to flush the imaged cavity.

In another embodiment, the buttons are implemented on a console, tablet (e.g., iPad) or the like and controlled remotely. Thus, the endoscopic device may be fashioned without control features implemented directly thereon, and may instead be controlled via Bluetooth, infrared remote, etc.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A medical system comprising:
a medical device including a handle and a shaft extending distally from the handle, the handle comprising:
   a pull wheel coupled to a first pull wire and a second pull wire, wherein the first pull wire and the second pull wire extend through the shaft to a distal tip of the shaft, and wherein the pull wheel is configured to apply tension to at least one of the first pull wire or the second pull wire to deflect the distal tip of the shaft;
   a motor coupled to the pull wheel and configured to rotate the pull wheel in response to a signal; and
   a first communication interface; and
an accessory device including a second communication interface configured to connect with the first communication interface and a carrier configured to couple to an end effector device, wherein the carrier is configured to move within a channel of the accessory device to actuate the end effector device, and
wherein the first communication interface of the medical device is configured to provide power to the accessory device.

2. The medical system of claim 1, wherein the motor includes a rotatable shaft coupled to the pull wheel.

3. The medical system of claim 1, wherein the pull wheel includes a first pull wire attachment coupled to the first pull wire and a second pull wire attachment coupled to the second pull wire.

4. The medical system of claim 1, wherein the handle includes an actuator coupled to the motor and configured to generate the signal.

5. The medical system of claim 4, wherein the actuator includes a knob or a button pad.

6. The medical system of claim 4, wherein the actuator includes a knob configured to rotate independently of movement of the pull wheel.

7. The medical system of claim 4, wherein the actuator is configured to rotate the pull wheel a predefined angular extent.

8. The medical system of claim 1, wherein the accessory device includes a motor coupled to the carrier and configured to move the carrier within the channel.

9. A medical system comprising:
a medical device including a handle connected to a shaft having a deflectable distal tip and a working channel, the handle comprising:

a pull wheel coupled to a first pull wire and a second pull wire, wherein each of the first pull wire and the second pull wire extends through the shaft to the distal tip;
   a motor coupled to the pull wheel and configured to rotate the pull wheel to deflect the distal tip in response to a signal;
   an actuator coupled to the motor and configured to generate the signal; and
   a first communication interface; and
an accessory device including a body, wherein the body includes a second communication interface coupled to the first communication interface and a carrier configured to couple to an end effector device, wherein the carrier is configured to move within a channel of the body to actuate an end effector of the end effector device, wherein a portion of the end effector device is configured to be received within the working channel of the shaft, and
wherein the first communication interface of the medical device is configured to provide power to the accessory device.

10. The medical system of claim 9, wherein the motor includes a rotatable drive shaft coupled to the pull wheel.

11. The medical system of claim 9, wherein the body includes a motor and a shaft, and wherein the motor of the body is configured to rotate the shaft of the body to move the carrier within the channel.

12. The medical system of claim 9, wherein the actuator includes a button pad configured to control the motor of the handle and the motor of the body.

13. A medical system comprising:
a medical device including a handle and a shaft extending distally from the handle to a distal tip, the handle comprising:
   a pull wheel coupled to a first pull wire and a second pull wire, wherein the first pull wire and the second pull wire extend through the shaft and to the distal tip;
   a motor including a rotatable shaft coupled to and configured to rotate the pull wheel to deflect the distal tip of the shaft;
   a first actuator coupled to the motor; and
   a second actuator operably coupled to the distal tip of the shaft, the second actuator being configured to manually deflect the distal tip of the shaft;
   one or more first communication interfaces; and
an accessory device including a second communication interface configured to connect with a corresponding first communication interface of the one or more first communication interfaces of the medical device, wherein the accessory device includes a carrier configured to move within a channel of the accessory device.

14. The medical system of claim 13, wherein the accessory device includes a motor coupled to the carrier and configured to move the carrier within the channel.

15. The medical system of claim 14, wherein the first actuator includes a button pad and the second actuator includes a knob.

16. The medical system of claim 15, wherein the first actuator is configured to control the motor of the handle and the motor of the accessory device.

* * * * *